United States Patent [19]

Girardot et al.

[11] Patent Number: 5,447,536
[45] Date of Patent: Sep. 5, 1995

[54] METHOD FOR FIXATION OF BIOLOGICAL TISSUE

[75] Inventors: Jean-Marie Girardot; Marie-Nadia Girardot, both of Dunwoody, Ga.

[73] Assignee: Biomedical Design, Inc., Atlanta, Ga.

[21] Appl. No.: 198,145

[22] Filed: Feb. 17, 1994

[51] Int. Cl.$^6$ ............................................. A61F 2/02
[52] U.S. Cl. ........................................ 8/94.11; 8/94.33; 530/356; 623/1; 623/2; 623/3; 623/11; 523/113
[58] Field of Search ............... 8/94.11, 94.1 R, 94.33, 8/94.21, 94.18, 94.19 C; 530/356; 623/1, 2, 3, 11, 12, 66; 427/2; 523/113

[56] References Cited

U.S. PATENT DOCUMENTS

| | | | |
|---|---|---|---|
| 4,378,224 | 3/1983 | Nimni et al. | 8/94.11 |
| 4,383,832 | 5/1983 | Fraefel et al. | 8/94.11 |
| 4,770,665 | 9/1988 | Nashef | 8/94.11 |
| 4,883,864 | 11/1989 | Scholz | 530/356 |
| 4,976,733 | 12/1990 | Girardot | 623/11 |
| 5,002,566 | 3/1991 | Carpentier et al. | 623/2 |
| 5,080,670 | 1/1992 | Imamura et al. | 623/2 |
| 5,147,514 | 9/1992 | Mechanic | 204/157.68 |

OTHER PUBLICATIONS

Daminik, "Structure and Properties of Crosslinked Dermal Sheep Collagen", *Bioplex Medical BV, Vaals, Nederland,* Chapters 7 and 8, Apr. 1993.

Harasaki et al., "Cross-Linking Agents, Degree of Cross-Linking and Calcifiability in Bioprosthetic Heart Valves", *Soc. for Biomaterials,* 16th Annl. Meeting, p. 25, May 20-23, 1990.

Eybl, et al., "Toxic effects of aldehydes released from fixed pericardium on bovine aortic endothelial cells," *J. Biomed. Mater. Res.* 23:1355-1365 (1989). No Month Available.

Nimni, et al., "Chemically modified collagen: A natural biomaterial for tissue replacement," *J. Biomed. Mater. Res.* 21:741-771 (1987). No Month Available.

Pereira, et al., "Effect of alternative crosslinking methods on the low strain rate viscoelastic properties of bovine pericardial bioprosthetic material," *J. Biomed. Mater. Res.* 24:345-361 (1990). No Month Available.

*Primary Examiner*—Prince Willis, Jr.
*Assistant Examiner*—Alan D. Diamond
*Attorney, Agent, or Firm*—Fitch, Even, Tabin & Flannery

[57] ABSTRACT

A process is provided for the non-glutaraldehyde fixation of a prosthesis to be implanted in a mammal whereby the prosthesis is fixed by employing cross-linking agents to form amide linkages between and within the molecules of the prosthetic tissue. The disclosed process prevents or retards calcification and results in a product which does not cause inflammation and is non-toxic; it thus provides prostheses that are well-suited for implantation in a mammal.

14 Claims, No Drawings

METHOD FOR FIXATION OF BIOLOGICAL TISSUE

The present invention relates to a process for fixing biological tissue prior to implantation into a mammal, and more particularly to a fixation process which creates amide linkages between and within the molecules of the biological tissue thereby producing tissues resistant to calcification. In addition, the resulting tissue is not toxic and does not elicit inflammatory responses after implantation.

BACKGROUND OF THE INVENTION

The surgical implantation of prosthetic devices (prostheses) into humans and other mammals has been carried out in recent years with increasing frequency. Such prostheses include, by way of illustration only, heart valves, vascular grafts, urinary bladders, left ventricular-assist devices, hip prostheses, silastic breast implants, tendon prostheses, and the like. They may be constructed from natural tissues, inorganic materials, synthetic polymers, or combinations thereof. By way of illustration, mechanical heart valve prostheses typically are composed of rigid materials, such as polymers, carbons and metals and employ one or more occluders which respond passively with changes in intracardiac pressure or flow. Natural tissue heart valve prostheses, on the other hand, typically are fabricated from either porcine aortic valves or bovine pericardium; in either case, the tissue is normally pretreated with glutaraldehyde and then sewn onto a flexible metallic alloy or polymeric stent which subsequently is covered with a poly(ethylene terephthalate) cloth sewing ring covering. Typically, the assembled prostheses (known to those of skill in the art as bioprostheses) are then stored in 0.2 percent glutaraldehyde.

Bioprostheses, that is prostheses derived from natural tissues, may be preferred over mechanical devices because of certain significant clinical advantages; for example, bioprostheses generally do not require routine anticoagulation. Moreover, when they fail, they usually exhibit a gradual deterioration which can extend over a period of months, or even years. Mechanical devices, on the other hand, generally require regular anticoagulation therapy and very occasionally undergo catastrophic failure; however, they do have other advantageous features.

Bioprostheses must be treated, prior to implantation into an animal different from the donor animal, in order to stabilize the tissue. This process of stabilization is known in the art as fixation. In 1968, Nimni et al. demonstrated that collagenous materials, the major component of bioprostheses, can be fixed by treating them with aldehydes. (Nimni et al., *J. Biol. Chem.* 243:1457–1466 (1968).) Later, it was discovered that, of various aldehydes tested, glutaraldehyde best retards degeneration of collagenous tissue. (Nimni et al., *J. Biomed. Mater. Res.* 21:741–771 (1987); Woodroof, E. A., *J. Bioeng.* 2:1 (1978).) Generally, the fixation process operates by blocking reactive molecules on the surface of and within the donor tissue, thereby rendering it substantially non-antigenic and suitable for implantation. Thus, the process of glutaraldehyde-fixation has been and continues to be applied to most all varieties of experimental and clinical bioprostheses.

Early experimental and clinical studies of glutaraldehyde-preserved bioprostheses were of bioprosthetic heart valves. The data compiled from these early studies demonstrated the excellent biomechanical properties, high resistance to enzymatic degradation, excellent hemodynamic properties and minimal thrombogenicity of the glutaraldehyde-preserved heart valve. However, follow-up clinical studies questioned the long-term durability of glutaraldehyde-fixed valves due to a variety of problems such as cuspal infection, low-grade immune reactions, severe calcification, stenosis and biodegradation. Further, it was discovered that the glutaraldehyde-fixation process induces toxic reactions due to the slow release of glutaraldehyde from the implanted tissue. These toxic reactions may be partially responsible for the immune reactions and the lack of endothelial cell coverage also found in these implants.

Calcification, which causes prosthesis degeneration, is an especially significant disadvantage to the use of tissue-derived prostheses. Indeed, cuspal calcification accounts for over 60 percent of the failures of cardiac bioprosthetic valve implants, such failures being substantially more frequent in children than in adults. Despite the clinical importance of the problem, the pathogenesis of calcification is incompletely understood. It seems that calcification is related to the extent of glutaraldehyde-induced cross-links and results from intrinsic and extrinsic mineralization in and on the surface of the bioprosthesis. (Schoen, F., *J. Card. Surg.* 2(1):65 (1987).) Further there is evidence of a specific calcium-binding amino acid, laid down after implantation of glutaraldehyde-preserved porcine bioprostheses, which has been postulated to play a role in calcification. (U.S. Pat. No. 4,770,665)

Efforts at retarding the calcification of bioprosthetic tissue have been numerous in recent years. The techniques resulting from these efforts may be broadly divided into two categories; those involving the pre- or post-treatment of glutaraldehyde-fixed tissue with one or more compounds that inhibit calcification (or modify the fixed tissue to be less prone to calcification) and those involving the fixation of the tissue with compounds other than glutaraldehyde, thereby reducing calcification.

The former category of techniques includes, but is not limited to, treatment with such compounds as:

a) detergent or surfactant, after glutaraldehyde fixation;

b) diphosphonates, covalently bound to the glutaraldehyde-fixed tissue or administered via injection to the recipient of the bioprosthesis or site-specifically delivered via an osmotic pump or controlled-release matrix;

c) amino-substituted aliphatic carboxylic acid, covalently bound after glutaraldehyde-fixation;

d) sulfated polysaccharides, especially chondroitin sulfate, after glutaraldehyde fixation and preferably followed by treatment with other matrix-stabilizing materials;

e) ferric or stannic salts, either before or after glutaraldehyde fixation;

f) polymers, especially elastomeric polymers, incorporated into the glutaraldehyde-fixed tissue; or g) water-soluble solutions of a phosphate ester or a quaternary ammonium salt or a sulfated higher aliphatic alcohol, after glutaraldehyde-fixation.

The latter category of techniques for reducing the calcification of bioprosthetic tissue, i.e., techniques involving the fixation of the tissue with compounds other than glutaraldehyde, includes but is not limited to, the following:

a) treatment by soaking the bioprosthetic tissue in an aqueous solution of high osmolality containing a photo-oxidative catalyst and then exposing said tissue to light, thereby fixing the tissue via photo-oxidization; and b) fixation via treatment with a polyepoxy compound, such as polyglycidyl ether (polyepoxy) compound.

In most cases, investigations related to glutaraldehyde-associated symptomatology have been limited to specific problems such as calcification and have not addressed the entire spectrum of symptoms. Thus, while the problem of calcification of glutaraldehyde-fixed bioprostheses has received a great deal of attention, the proposed solutions have generally failed to address any other complications presented by the presence of glutaraldehyde, such as toxicity, immune reactions and degeneration. Glutaraldehyde released from the tissue is cytotoxic and prevents the formation of endothelial cell growth on the bioprosthesis necessary for long-term durability. This persistent damage to the implant and surrounding tissue due to the long-term slow release of glutaraldehyde may be fully eradicated only by using a fixation process that does not include glutaraldehyde. The complexity and gravity of the clinical problems resulting from glutaraldehyde-preserved bioprostheses warrant the search for an alternative fixation method.

SUMMARY OF THE INVENTION

Accordingly, the present invention provides a method for the non-glutaraldehyde fixation of a prosthesis to be implanted in a mammal whereby said prosthesis is fixed by forming amide linkages between and within the molecules of the prosthetic tissue. Also, the invention provides prostheses, suitable for implantation in a mammal, made by the aforesaid method.

In one preferred embodiment, di- or tri- carboxylic acids and di- or tri-amines of about six to about eight carbon atoms in length, are used, in a sequential manner, to form amide cross-links. In a particularly preferred embodiment, suberic acid, a di-carboxylic acid, and 1,6-hexane diamine are used to form the amide linkages, resulting in cross-linking chains of about six to about twenty-four carbon atoms in length between and within the molecules of the tissue of the prosthesis.

The method of the present invention is useful for preventing or retarding the calcification of a prosthesis implanted in a mammal, such as a human, and it provides a product that does not cause an inflammatory response in the body and is nontoxic. It has particular application with respect to those prostheses which are normally fixed using glutaraldehyde and more particularly, to those prostheses which are especially susceptible to degeneration as a result of calcification.

DETAILED DESCRIPTION OF THE INVENTION

As used herein, the term "prosthesis" is meant to include any prosthesis which is derived in whole or part from animal or other organic tissue and which is to be implanted in a mammal. Thus, the term generally includes bioprostheses, such as heart valves and other heart components, vascular replacements or grafts, heart replacements, urinary tract and bladder replacements, bowel and tissue resections in general, and the like. However, it will be recognized by those having ordinary skill in this art that the present invention may be of most importance in relation to prostheses for which glutaraldehyde release and resultant toxicity, degeneration and/or calcification after implantation has been a clinical problem. Thus, while the present invention can be used with essentially any bioprosthesis, it may not be as beneficial for a prosthesis which is not normally fixed using glutaraldehyde or is not otherwise likely to suffer degeneration or malfunction as a result of mineralization.

The fixation process described herein relies on the availability of free active moieties on and within the prosthetic tissue that are capable of forming amide bonds with the cross-linking agent(s); for example, carboxyl and amine moieties. Thus, the prosthesis will be one which is made from natural tissues, including but not limited to bovine, ovine, porcine and possibly even human tissue. Other natural materials, well known to those having ordinary skill in the art, also can be used.

The term "cross-link" is defined as understood by those of skill in the art. Generally, where biological tissue is concerned, cross-linking refers to the process of forming covalent bonds (or cross-links) either directly between free active moieties on or within the tissue or between the free active moieties of the tissue and one or more compounds (or cross-linking agents), in such a manner as to leave few or no active moieties on or within the tissue. This cross-linking process "fixes" or stabilizes the tissue by making the tissue less antigenic and thus less susceptible to degradation than before the process.

Thus the term "fixation" as used herein, and as generally understood by those of skill in the art, refers to the process of treating biological tissue in order to stabilize it for implantation in a host animal different from the donor individual. Currently, most bioprosthetic tissue is fixed via treatment with glutaraldehyde.

In general, a "cross-linking agent or reagent", as used herein, is a compound capable of covalently binding to the free active moieties of prosthetic tissue and/or to other cross-linking agents in such a manner as to result in cross-links between and within the molecules of the prosthetic tissue and between the molecules of the prosthetic tissue and the agent, thereby fixing said tissue. The cross-linking agent(s) is selected in such a way as to maximize fixation of the tissue being treated while minimizing the risk of damage to the prosthesis during treatment and minimizing the risks, such as of toxicity, inflammation, calcification, etc., to the host animal in whom the treated prosthesis is to be implanted. The cross-linking agents are preferably water-soluble so that aqueous buffers may be utilized thereby minimizing the risk of damage to the prosthesis during the fixation process.

Further, the cross-linking agents or reagents have at least two reactive moieties sufficiently distant from each other to permit covalent binding, at at least two locations, between itself and the prosthetic tissue and/or another cross-linking agent. Preferably, the reactive moieties on any one cross-linking agent are the same and bind via formation of amide bonds. Also preferably, the cross-linking agents are chains from about 4 to about 24 carbon atoms in length and most preferably from about 6 to 8 carbon atoms in length. The reactive moieties are preferably separated by a chain of at least 4 carbon atoms (more preferably at least 6) and are preferably located at the respective ends of the longest carbon chain. One or more cross-linking agents may be used, and preferably, at least two different agents will be used. In one preferred embodiment, either a di- or tri-amine and either a di- or tri-carboxylic acid are used as the two cross-linking agents.

The cross-linking agents may be straight-chained or branched-chained, appropriately substituted compounds. Preferably they are straight chains having the reactive moieties or groups at each terminus. Except for the substituent through which covalent linking to the prosthesis or another cross-linking agent is achieved, the nature and number of the substituents are not critical, provided that they do not induce calcification or other adverse physiological effects upon implantation; do not create non-water-soluble or toxic by-products; and do not adversely effect the compound's water solubility. Preferably, any such substituents should assist to stabilize the tissue.

The concentration of each cross-linking agent can vary and will depend on the nature of the cross-linking agent, for example, the efficiency with which it binds to the prosthetic tissue and/or another cross-linking agent. In certain preferred embodiments, concentrations ranging from about 5 mM (millimolar) to about 20 mM are used; however, one skilled in the art can readily determine appropriate concentrations for each cross-linking agent.

The terms "coupling agent" and "coupling enhancer", as used herein, refer to reagents that respectively, initiate and enhance the cross-linking reaction between cross-linking agents and/or between prosthetic tissue and a cross-linking agent. Those of skill in the art will be familiar with which such reagents are most effective with which cross-linking agents. In a preferred embodiment, 1-ethyl-3(3-dimethyl aminopropyl)carbodiimide hydrochloride (EDC) and N-hydroxysulfosuccinimide (sulfo-NHS) are the coupling agent and coupling enhancer, respectively. The concentration of the coupling agent and coupling enhancer can vary and will depend on such things as the cross-linking agent employed. Appropriate concentrations are readily determinable by those of skill in the art.

Reaction conditions for the cross-linking of the prosthesis tissue may vary, depending on the cross-linking agents and cross-linking chemistry employed. In general, the cross-linking process is carried out in an aqueous solution buffered at a suitable pH. A suitable buffer is used, and buffers from among those well known to those of ordinary skill in this art are chosen so as to best suit the cross-linking agents being employed. Examples of suitable buffers include, but are not limited to, N-2-Hydroxyethylpiperazine-N'-ethanesulfonic acid (HEPES) and 3-(N-morpholino)propanesulfonic acid (MOPS), and the like. For additional details on buffers, see, e.g., Gerald D. Fasman, Editor, "*CRC Handbook of Biochemistry and Molecular Biology,*" 3rd Edition, Physical and Chemical Data Volume I, CRC Press, Inc., Boca Raton, Fla., 1976, pp 354–377. The buffer concentration is not critical and can vary fairly widely.

The pH of the buffer also can vary, again depending upon the cross-linking agents to be employed. In preferred embodiments, the buffer concentration and pH are chosen to be the least harmful to the prosthetic tissue and cross-linking agents and the most effective for the cross-linking reaction; for example, a preferred embodiment employs a HEPES buffer at a pH from about 6.5 to about 7.4. All solutions are filtered before use, for example, through 0.45 μm Acrodisc TM filters.

The prosthetic tissue to be fixed by the cross-linking method herein described is preferably freshly obtained from the donor animal and immediately processed. For example, the tissue is rinsed or washed in an appropriate aqueous solution to remove red blood cells and other contaminating debris. In preferred embodiments, ice cold 0.85% saline solution is used. Those of skill in the art will readily recognize alternative, equivalent solutions for this cleaning. If the tissue is stored, for example overnight, it is stored in an appropriate buffer as described further below, at an appropriate, lower temperature such as about 4° C.

After processing as described above, the prosthetic tissue is incubated with a cross-linking agent, a coupling agent and a coupling enhancer. Incubation time can vary and will depend upon such things as the particular cross-linking agents, coupling agent and coupling enhancer employed, as well as the conditions of cross-linking such as concentrations of agents, pH and temperature. In preferred embodiments, the incubation time is about 48 hours. The cross-linking agent is chosen as previously described, preferably, such that the active moieties on the agent readily covalently bind, via amide bonds, to the prosthetic tissue. For example a cross-linking agent with either multiple active carboxyl or multiple amine moieties is particularly preferred. Because the reactions described herein are for the cross-linking of bioprosthetic tissue, the temperature of reaction typically will not exceed 40° C. nor fall below 0° C., and preferably, reaction is carried out at room temperature.

This first coupling reaction results in a cross-linking agent being covalently bound to the prosthetic tissue by one or more of its reactive moieties. Most molecules of cross-linking agent will be bound (or anchored) to the tissue via one reactive moiety with the other moiety(s) being either bound to the tissue or unbound and thus free for further reaction. After a sufficient incubation time as described above, the tissue is rinsed or washed in aqueous buffer to remove non-reacted and water-soluble by-products. Appropriate buffers are used as previously described and as understood by those of skill in the art. The bioprosthetic tissue is not permitted to dry, rather it is maintained in the buffer solution.

Further cross-linking is accomplished in the same manner as just described by using a second cross-linking agent that is capable of covalently binding, preferably via amide bond formation, to the first cross-linking agent and optionally to the prosthetic tissue. This results in the second cross-linking agent being bound, via one or more of its reactive moieties, to an unbound moiety of the first cross-linking agent or to the prosthetic tissue or to both. Thus, carbon atom chains of various lengths are formed between and within the prosthetic tissue. Additional coupling reactions are performed as necessary to effectively fix the prosthetic tissue. In preferred embodiments, the fixation process is considered to be complete after three such coupling reactions. In a particularly preferred embodiment, the third cross-linking agent which is used is of the same composition as the first cross-linking agent.

The method of fixation described herein, whereby water-soluble cross-linking agents of between about 4 and about 24 carbon atoms in length are coupled to bioprosthetic tissue, results in a myriad of links (or bridges) of cross-linking agents between and within the molecules of the prosthetic tissue having reactive moieties. Fixation is complete when few if any reactive moieties remain unreacted on the tissue's surface or just within the tissue. Some short links will be comprised of a single molecule of a cross-linking agent bridging two reactive moieties located on or within the prosthetic tissue; however, it is believed that a major portion of the links in the prosthetic tissue will be comprised of two or more cross-linking agents connected to each other.

The preferred embodiments of cross-linking agents have carbon chains which contain multiple carboxylic acid or amine reactive moieties which form amide bonds with one another. The prosthetic tissue is also capable of forming amide bonds with both of these preferred cross-linking moieties because of the presence of reactive carboxyl and amine groups on and within the tissue.

The present invention is further described by the examples which follow. Such examples, however, are not to be construed as limiting in any way either the spirit or the scope of the present invention. In the examples, percentages are percents by volume or of weight per unit volume, e.g., grams per liter, and all temperatures are in degrees Celsius, unless otherwise specified.

EXAMPLE 1

A process embodying feature of the present invention is illustrated by the formation of amide linkages between and within porcine aortic valve tissue by the sequential coupling of a di-carboxylic acid and a di-amine to molecules forming this tissue.

I. Preparation of Porcine Tissue

Fresh porcine hearts were obtained from a slaughterhouse, on ice, 24 hours after slaughter and immediately processed. The aortic valve leaflets and wall specimens (1×3.5 cm coupons) were dissected and rinsed 6 times in ice-cold 0.85% saline to remove red blood cells and other debris. They were then stored overnight at 4° C. in 10 mM HEPES, 0.85% NaCl, pH 6.5 (HEPES buffer).

II. Cross-linking of Porcine Aortic Valve Tissue

A. Addition of First Cross-linking Agent

Twenty-five leaflets and three wall coupons were transferred from the HEPES buffer to 75 ml of the first cross-linking agent, 10 mM suberic acid (98%, purchased from Aldrich), prepared in HEPES buffer. A twenty-five ml solution of a coupling agent, 200 mM 1-ethyl-3(3-dimethyl aminopropyl) carbodiimide hydrochloride (EDC), together with a coupling enhancer, 10 mM N-hydroxysulfosuccinimide (sulfo-NHS) (obtained from Sigma and Pierce, respectively) in HEPES buffer, prepared immediately prior to use, was then added to the solution to initiate the cross-linking reaction. The jar containing the reagents, leaflets and wall coupons was incubated for 48 hours at room temperature. The samples were then rinsed once with 50 ml of HEPES buffer to eliminate non-reacted and water soluble by-products of the reaction. At this point, the suberic acid is covalently bound to free amine groups of the collagenous tissue. Some of the acid molecules may bridge two tissue amine groups, but most of them will be anchored to one amine moiety, leaving one carboxyl group free and available for further reaction.

B. Addition of Second Cross-Linking Agent

Next, the valve leaflets and wall coupons were transferred to a 75 ml solution of the second cross-linking agent, 15 mM 1,6-hexane diamine (98%, purchased from Aldrich), prepared in HEPES buffer. The cross-linking reaction was carried out as described above; that is, addition of EDC/sulfo-NHS, incubation for 48 hours at room temperature, and then a single HEPES buffer rinse. This second coupling reaction results in chains of six, eight, fourteen or even twenty-two carbon atoms in length between and within the collagenous molecules of the tissue samples, with a large portion of the second cross-linking agent having one amine group free for further reaction.

C. Addition of Third Cross-Linking Agent

As the third and final cross-linking agent, 10 mM suberic acid was again applied to the leaflets and wall coupons, using the same conditions as described for the first coupling reaction. Once this final coupling reaction was complete, the tissue samples were rinsed in HEPES buffer and stored until use at room temperature in HEPES buffer pH 7.4 containing 20% isopropanol.

EXAMPLE 2

An alternative fixation process is carried out by the formation of amide linkages between and within porcine aortic heart valve tissue by the initial coupling of a diamine, followed by the coupling of a di-carboxylic acid to this tissue. Twenty-five leaflets and three wall coupons were obtained from fresh porcine hearts, and treated as described in Example 1, save that the cross-linking agent employed, in steps IIA. and C. was 1,6-hexane diamine, and the cross-linking agent employed in step IIB. was suberic acid.

EXAMPLE 3

A further alternative fixation process is carried out by the formation of amide linkages between and within porcine aortic heart valve tissue by the initial coupling of a diamine followed by coupling of a tri-carboxylic acid to this tissue. Twenty-five leaflets and three wall coupons were obtained from fresh porcine hearts and treated as described in Example 2, save that, instead of suberic acid, 7 mM 1,3,5-benzenetricarboxylic acid (98%, purchased from Aldrich), prepared in HEPES buffer was used as the second cross-linking agent.

EXAMPLE 4

A still further fixation process is carried out by the formation of amide linkages between and within porcine aortic heart valve tissue by the initial coupling of a tri-carboxylic acid followed by coupling of a diamine to this tissue. Twenty-five leaflets and three wall coupons were obtained from fresh porcine hearts and treated as described in Example 1, save that as the first and third cross-linking agents, in steps IIA. and C., 7 mM 1,3,5-benzenetricarboxylic acid (98%, purchased from Aldrich), prepared in HEPES buffer, was employed.

Characterization and Comparison of Treated Tissue and Various Control Tissues The porcine aortic valve tissue treated as described in Examples 1 to 4, inclusive, together with two controls and a comparison group, were characterized and compared. The control groups included an "EDC control" of porcine aortic valve tissue treated as described in Example 1, save that HEPES buffer was used in place of the cross-linking agents, and a "fresh tissue control" of porcine aortic valve tissue stored in HEPES buffer containing 20% isopropanol. Also, a "glutaraldehyde comparison" of tissue dissected from glutaraldehyde-fixed porcine aortic valves was used (provided by Medtronic, Heart Valves Division, Calif.).

I. Thermal Denaturation

A. Method

Three leaflets from each of Examples 1–4, the glutaraldehyde comparison and the above-described two controls were secured between one fixed and one rotating alligator clip attached to a reading needle providing a 5-fold length amplification. They were then immersed in distilled water at 45° C. The water temperature was then increased at a rate of 1.5° C. per minute. The temperature at which the tissue started to contract was recorded as the shrinkage temperature and expressed as mean ±SEM° C. shrinkage temperature.

B. Results

The shrinkage temperatures of leaflets fixed using processes set forth in Examples 1 through 4 as well as the shrinkage temperature of the EDC control were all higher than the shrinkage temperature of the glutaraldehyde comparison, which was higher than the shrinkage temperature of the fresh tissue control. Shrinkage temperature (or point of thermal denaturation) is directly related to the density of cross-linking on and within the molecules of the tissue. Thus, fixation of the tissue by the process of Examples 1–4 confers at least as great if not greater cross-linking density to the tissue than does fixation by the glutaraldehyde method. The shrinkage temperature of the EDC control is as high as that of glutaraldehyde and suggests that EDC alone induces cross-linking between close residual carboxyl and amine moieties located within the tissue itself.

II. Residual Amine Test

A. Methods

Three half leaflets and 3 wall coupons from each of Examples 1–4, the glutaraldehyde comparison and the controls were incubated at 95° C. for 20 minutes in 1 ml of ninhydrin in citrate buffer, pH 5.0. They were cooled to room temperature, then removed from their incubation solutions, dried and weighed. The incubation solutions were diluted with 1 ml of 50% (v/v) isopropanol in distilled water. The optical absorption was determined at 570 nm using a Beckman DB-G spectrophotometer. A standard curve was established using L-norleucine at concentrations ranging from 0 to 100 nM/ml. The results are expressed as nanomoles of 1-norleucine amine equivalent per mg of dry tissue and are compared.

B. Results

The relative differences between conditions were similar for the cusps and the walls. The level of residual amines was significantly lower for all fixed tissue (Examples 1–4, glutaraldehyde comparison and EDC control) than for the fresh tissue. The levels were not significantly different between the glutaraldehyde comparison and the samples from Examples 1 and 4. A higher level of residual amines was observed in the samples from Examples 2 and 3 as compared to the glutaraldehyde comparison. This was probably due to the residual amines resulting from the diamine treatment of the third coupling reaction. The low level of residual amines observed in the EDC control, as compared with the fresh tissue control, was a reflection of the fact that treatment of the tissue with EDC in the absence of cross-linking agents results in the modification of approximately 63% of the amines and thus allows partial cross-linking of the tissue, as was also reflected in the shrinkage temperature study, above. Thus, as a measurement of the degree of fixation of the tissue, the residual amine test suggests that the fixation processes in Examples 1–4 are as efficient as the glutaraldehyde method.

III. Collagenase Digestion

A. Methods

A collagenase solution was prepared by dissolving 5 mg collagenase, 180 mg $CaCl_2.2H_2O$ and 65 mg sodium azide in 130 ml of HEPES buffer, pH 7.4. Three half-leaflets and three wall coupons from each of Examples 1–4, the glutaraldehyde comparison and the controls were dried for 1 hour at room temperature, individually minced, weighed and incubated in 3 ml of the collagenase solution at 37° C. for 72 hours in an orbital shaker set at 150 rpm. The levels of amines released from the samples were determined by the ninhydrin test described in the residual amine test above, using 0.1 ml of collagenase solution free of particulate material in 1 ml of ninhydrin in citrate buffer solution pH 5.0. The results are expressed as nanomoles of 1-norleucine amine equivalent per mg of dry tissue and compared.

B. Results

The fresh tissue control sample showed in excess of 350 nanomoles amine equivalent per mg dry tissue released and had no resistance to collagenase whereas the samples from each of Examples 1–4, as well as the EDC control and glutaraldehyde comparison, were fully resistant to digestion. Thus, the fixation processes of Examples 1–4 result in tissue that is as resistant to collagenase digestion as the glutaraldehyde-fixed tissue.

IV. Protease Digestion

A. Methods

A protease solution was prepared by dissolving 75 mg of protease and 75 mg $CaCl_2.2H_2O$ in 150 ml of HEPES buffer pH 7.4, containing 50 mM glycine. Three half-leaflets and three wall coupons from each of the four examples and the controls were blotted and weighed. In order to obtain the dry weight of the samples prior to protease digestion, a piece (25%) of each blotted sample was cut, dried and weighed. The ratio of blotted weight/dry weight was then used to calculate the dry weight of the specimens prior to protease digestion. The remaining 75% of the samples were incubated in 3 ml of protease solution at 50° C. for 22 hours. They were then removed from the protease solution, dried and weighed. The weight loss corresponds to proteolytic degradation, and the results are expressed as % weight decrease after 22 hours of incubation.

B. Results

The fresh tissue control leaflets and walls were completely digested by the nonspecific protease during 22 hours of incubation. The leaflets from Examples 1–4 inclusive and the EDC controls resisted digestion as well as the glutaraldehyde-fixed leaflets. The walls from Examples 1–4 and the EDC controls showed greater resistance to protease digestion than did the glutaraldehyde comparison walls. Therefore, based on this protease digestion test, tissues fixed according to Examples 1–4 are at least as well, if not better, cross-linked than glutaraldehyde-fixed tissues.

V. Calcification

An important advantage offered by the present invention is illustrated by a comparison of the calcium levels of the treated and control tissues after implantation subdermally in rats.

A. Method

Twelve half-leaflets and three wall coupons from each of Examples 1–4 and from the glutaraldehyde-fixed and EDC control groups were washed 3 times in saline and implanted subdermally in the abdominal area (4 implants per animal) of 3 week-old male Sprague Dawley rats. Six half-leaflets and the 3 wall coupons per test group were retrieved after 4 weeks, and the remaining 6 half-leaflets per group were retrieved after 8 weeks. The surrounding tissue capsule was removed. The samples were washed 5 times in distilled water, lyophilized, weighed and hydrolyzed in 1 ml of ultra-pure 6N HCl at 85° C. for 24 hours. The hydrolysates were dried under vacuum and the residues resuspended in 0.3N HCl. Calcium levels were determined by the Inductively Coupled Plasma analysis method using a Perkin Elner 8000 ICP spectrophotometer at Georgia Tech Research Institute. The results are expressed as milligrams of calcium per gram of dry tissue.

B. Results

The following Table 1 illustrates the significant difference between the minimal calcification of the tissues fixed using the processes of Examples 1–4 and the high degree of calcification observed in the tissues fixed using the glutaraldehyde method, with the approximate average values for each being expressed.

TABLE 1

| Method of Fixation | Mean ± SEM (miligrams calcium/gram dry tissue) | | |
|---|---|---|---|
| | Leaflets implanted 4 weeks | Leaflets implanted 8 weeks | Walls implanted 4 weeks |
| Glutaraldehyde | 204 ± 10 | 230 ± 34 | 130 ± 8 |
| Example 1 | 9.5 ± 4.8 | 31 ± 21 | 35 ± 4 |
| Example 2 | 8.1 ± 5 | 19 ± 18 | 26 ± 14 |
| Example 3 | 4.2 ± 2,2 | 36 ± 13 | 33 ± 5 |
| Example 4 | 16 ± 6 | 6 ± 4 | 22 ± 8 |
| EDC control | 25 ± 15 | 21 ± 19 | 40 ± 8 |

As can be seen from the table, all the leaflets treated as per Examples 1–4 and the EDC control group were resistant to calcification. After implantation for eight weeks, the glutaraldehyde comparison samples were significantly more calcified than the leaflets cross-linked using the fixation processes of Examples 1–4. There was no significant difference in the calcium levels among the samples treated as per Examples 1–4 nor between 4 and 8 week implantation periods, which indicates that calcification does not increase with implantation duration in this model.

Glutaraldehyde-fixed walls were also significantly more calcified than walls treated as per Examples 1–4 and EDC controls. Because the calcification of the aortic wall of non-stented valves may be of clinical significance, this improved process of fixation offers significant advantages over the glutaraldehyde fixation method, because the need for antimineralization treatment before implantation may be eliminated.

VI. Histology

Histological studies were performed before and after implantation on aortic valve leaflets fixed according to Examples 1–4 and on glutaraldehyde-fixed leaflets.

A. Methods

1) Scanning Electron Microscopy.

Three leaflets from each of Examples 1–4 and from the glutaraldehyde treatment were cut transversely to expose the internal layers (fibrosa, spongiosa and ventricularis) of the tissue. The samples were then critically point dried in ethanol, coated with AUPd and examined using a Hitachi S-800 field emission scanning electron microscope at 15 Kv. The three structures of interest, inflow and outflow surfaces and internal layers, were scanned and representative areas were photographed.

2) Light Microscopy

From each of Examples 1–4 and each control, three unimplanted half-leaflets and three half-leaflets previously implanted subcutaneously in rats for 4 weeks were placed in 4% glutaraldehyde and sent to Dr. Frederick Schoen, Brigham and Women's Hospital, Boston, Mass. The samples were embedded in JB-4 glycol methacrylate medium (Polysciences, Inc. Warrington, Pa.). Sections 2 to 3 $\mu$m thick were cut with glass knives and stained with hematoxylin and eosin, von Kossa's stain (for calcium phosphates) and the Movat pentachrome stain (for collagen, elastin and mucopolysaccharides).

B. Results

1) Scanning Electron Microscopy

The leaflets treated according to Examples 1–4 had normal morphology. The tissue is compact and without delamination. The inflow and outflow surfaces of the leaflets show no sign of roughening.

2) Light Microscopy

The evaluation of the histologic specimens according to the morphologic criteria of 1) "quality" of unimplanted tissue, 2) calcification during subcutaneous implantation in young rats, and 3) degree of inflammatory reaction to and invasion of the valve leaflet, suggests that tissues treated according to Examples 1–4 are as well preserved as the glutaraldehyde-fixed tissue, are resistant to calcification and do not elicit adverse inflammatory reaction.

VII. Biocompatiblity Study

A. Method

Twenty leaflets from Example 1, in 20% isopropanol in HEPES buffer were sent to Dr. James A. Anderson at Case Western University, Cleveland, Ohio. They were cut, sterilized, placed in small stainless steel wire mesh cages and implanted subdermally in rats. Empty cages served as controls. The degree of inflammatory response was determined at 4, 7, 14 and 21 days of implantation by quantitative and differential leukocyte, polymorphonuclear and macrophage counts, and alkaline and acid phosphatase analyses of the exudate that collected in the cages.

B. Results

The leaflets were found to be biocompatible and nontoxic. Thus, animal tissue fixed according to the fixation process of Example 1, when implanted in mammals, elicits no unusual immune responses from the host animal.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto. For example, if the initial treatment step is carried out using one dicarboxylic acid, although it is preferable to employ a third step and that such third step be carried out using the same dicarboxylic acid, a different dicarboxylic acid or a tricarboxylic acid could be alternatively employed in such third step. The foregoing similarly applies when a diamine is employed in the first treatment step.

Particular features of the invention are emphasized in the claims which follow.

What is claimed is:

1. A process for fixing animal tissue to render it suitable for implantation in living mammals, comprising the steps of:
   a) treating said animal tissue with a first cross-linking agent containing either at least two reactive amine moieties or at least two reactive carboxyl moieties, in the presence of a coupling agent, such that at least one reactive moiety forms an amide bond with a tissue molecule while another reactive moiety on at least some portion of said first cross-linking agent remains free; and
   b) repeating the treatment described in (a) with a second cross-linking agent containing at least two reactive carboxyl moieties, if the cross-linking agent used in (a) contains amine moieties, or vice-versa, such that amide bonds are formed at least between reactive moieties on one portion of said second cross-linking agent and said free moieties on said first cross-linking agent, resulting in the formation of links between or within the molecules of said animal tissue wherein some of said links are chains containing at least two of said cross-linking agents.

2. The process of claim 1 wherein step (a) is repeated after step (b) using a third cross-linking agent so as to create amide bonds (i) between one reactive moiety on one portion of said third cross-linking agent and free reactive moieties on said one portion of said second cross-linking agent and (ii) between another reactive moiety on said one portion of said third cross-linking agent and either a tissue molecule or a free reactive moiety on said second cross-linking agent, thereby increasing the number of said links formed between and within the molecules of said tissue.

3. The process of claim 2 wherein said cross-linking agents comprise water-soluble di- or tri-amines and water-soluble di- or tri-carboxylic acids.

4. The process of claim 3 wherein said cross-linking agents are each at least 4 carbon atoms in length.

5. The process of claim 1 wherein step (a) employs a di- or tri-amine, and step (b) employs a di- or tri-carboxylic acid.

6. The process of claim 1 wherein step (a) employs a di- or tri-carboxylic acid, and step (b) employs a di- or tri-amine.

7. The process of claim 1 wherein step (a) employs 1,6 hexane diamine, and step (b) employs suberic acid.

8. The process of claim 1 wherein step (a) employs suberic acid and step (b) employs 1,6 hexane diamine.

9. The process of claim 1 wherein step (a) employs 1,3,5-benzenetricarboxylic acid, and step (b) employs 1,6 hexane diamine.

10. The process of claim 1 wherein step (a) employs 1,6 hexane diamine, and step (b) employs 1,3,5-benzenetricarboxylic acid.

11. The process of claim 1 wherein step (a) employs 1,6 hexane diamine, and step (b) employs adipic acid or terephthalic acid.

12. The process of claim 1 wherein step (a) employs adipic acid or terephthalic acid and step (b) employs 1,6 hexane diamine.

13. A process for fixing animal tissue to render it suitable for implantation in living mammals, which process comprises the following steps:
   (a) treating said animal tissue with a water-soluble first reagent having at least 2 reactive amine moieties in the presence of a coupling agent such that said reactive amine moieties are promoted to form amide bonds with a tissue molecule;
   (b) washing said treated animal tissue to remove unreacted reagent;
   (c) treating said washed animal tissue with a second reagent containing at least 2 reactive carboxyl moieties in the presence of a coupling agent that promotes said reactive moieties to form amide bonds with a tissue molecule and with free reactive amine moieties on said first reagent; and
   (d) washing said twice-treated animal tissue to remove unreacted second reagent.

14. A process according to claim 13 wherein said twice-washed animal tissue is further treated with a third reagent containing at least 2 reactive amine moieties in the presence of a coupling agent that promotes said reactive amine moieties to form amide bonds, and then washing said further treated animal tissue to remove said unreacted third reagent.

* * * * *